(12) United States Patent
Mane et al.

(10) Patent No.: US 8,702,016 B2
(45) Date of Patent: Apr. 22, 2014

(54) METHOD AND DEVICE FOR RELEASING A PERFUME OR SCENT

(75) Inventors: Jean Mane, Grasse (FR); Louis Aguadisch, Valbonne (FR); Gilles Stalet, Grasse (FR)

(73) Assignee: V. Mane Fils, Bar sur Loup (FR)

( * ) Notice: Subject to any disclaimer, the term of this patent is extended or adjusted under 35 U.S.C. 154(b) by 0 days.

(21) Appl. No.: 13/205,103

(22) Filed: Aug. 8, 2011

(65) Prior Publication Data

US 2011/0290904 A1 Dec. 1, 2011

Related U.S. Application Data

(62) Division of application No. 12/159,393, filed as application No. PCT/FR2006/002862 on Dec. 22, 2006, now abandoned.

(30) Foreign Application Priority Data

Dec. 28, 2005 (FR) ..................... 05 13425

(51) Int. Cl.
*A61L 9/12* (2006.01)
(52) U.S. Cl.
CPC ........................ *A61L 9/12* (2013.01)
USPC .................. 239/34; 422/5; 422/120
(58) Field of Classification Search
CPC ........................................ A61L 9/12
USPC .......... 422/5, 120; 206/222; 220/521; 239/34
See application file for complete search history.

(56) References Cited

U.S. PATENT DOCUMENTS

| 3,006,347 | A | 10/1961 | Josiah |
| 3,869,554 | A | 3/1975 | Pittet |

(Continued)

FOREIGN PATENT DOCUMENTS

| EP | 0 317 658 A1 | 5/1989 |
| EP | 0 478 326 A1 | 4/1992 |
| EP | 1410753 | 4/2004 |
| RU | 2254277 | 6/2005 |

(Continued)

OTHER PUBLICATIONS

The Baltimore Sun Jun. 8, 2003 {http://articles.baltimoresun.com/2003-06-08/news/0306090407_1_turmeric-allergies-stinging-nettle}.

*Primary Examiner* — Sean E Conley
(74) *Attorney, Agent, or Firm* — Young & Thompson

(57) ABSTRACT

A method for masking or modifying the olfactory or gustatory sensation generated in a user by a base product (7) includes releasing an aromatic or fragrant composition over time in a sequenced manner in relation to the release of the base product (7), the aromatic or fragrant composition being housed in at least one rupturable container (5). A device used to implement the method is also disclosed.

12 Claims, 1 Drawing Sheet

(56) References Cited

U.S. PATENT DOCUMENTS

| | | | |
|---|---|---|---|
| 4,964,570 A * | 10/1990 | Haiduk | 239/36 |
| 5,053,051 A | 10/1991 | Tennigkeit et al. | |
| 5,154,842 A | 10/1992 | Walley | |
| 5,573,756 A | 11/1996 | Lambrechts | |
| 5,769,833 A | 6/1998 | Hasse | |
| 6,165,615 A * | 12/2000 | Itakura et al. | 428/407 |
| 6,238,690 B1 | 5/2001 | Kiefer | |
| 6,287,550 B1 | 9/2001 | Trinh et al. | |
| 6,348,218 B1 | 2/2002 | Hed et al. | |
| 6,673,301 B2 | 1/2004 | Cargile | |
| 2002/0066680 A1 | 6/2002 | Stern | |
| 2004/0017017 A1 | 1/2004 | Van Lengerich | |
| 2007/0023381 A1 | 2/2007 | Cerveny | |

FOREIGN PATENT DOCUMENTS

| | | |
|---|---|---|
| WO | 0125414 | 4/2001 |
| WO | 03/009711 A1 | 2/2003 |
| WO | 03009711 | 2/2003 |
| WO | 2004006967 | 1/2004 |
| WO | 2004089777 | 4/2004 |
| WO | 2005017085 A1 | 2/2005 |

\* cited by examiner

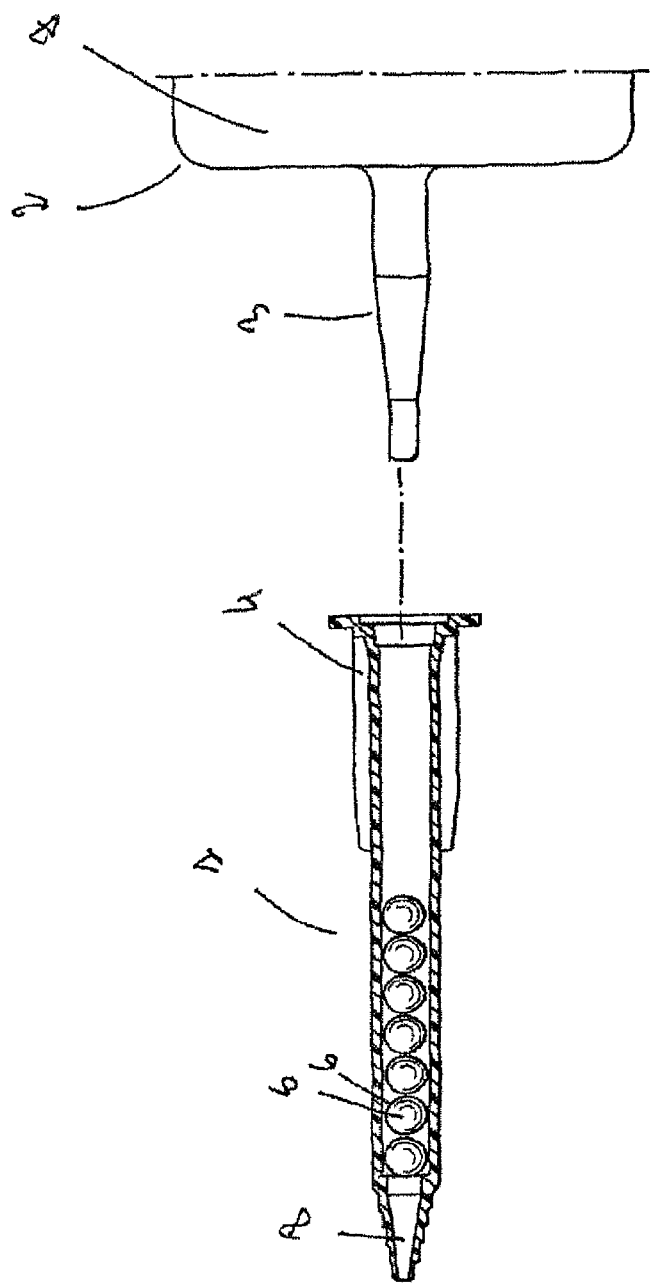

METHOD AND DEVICE FOR RELEASING A PERFUME OR SCENT

The invention relates to the field of perfumes, scents and fragrances, and more particularly a new delivery of an aromatic or fragrant composition designed to perfume or scent a base product, initially contained in a package.

There is a certain number of situations in which a base product cannot be perfumed before its final packaging; for example, because the base product is incompatible with the aromatic or fragrant composition, or because the mixture of the base product and the aromatic or fragrant composition adversely affects the stability of the base product; or else because the aromatic or fragrant composition is unstable; or else because it is not desired that the whole of the packaged base product is perfumed or scented, for reasons that may be medical, cosmetic or quite simply for reasons of taste.

For example, in cosmetics, the smell of ammonia involved in the composition of hair colorants is a disagreeable smell that requires being masked. Hair colorants usually consist of two preparations that are designed to be mixed extemporaneously just before use. The first preparation contains alkaline agents, such as ammonia or aminated alkaline agents, which allow the hair to swell, which helps with the penetration of the pigment; the second preparation contains oxidizing agents, for example hydrogen peroxide. Particularly because of the extreme volatility of ammonia, the masking of this unpleasant smell is difficult and is the subject of much research (see for example EP1346720). Another difficulty arises from the fact that the perfumes likely to mask this smell of ammonia are not always compatible with the alkalinity of the ammonia-containing composition in question, and this incompatibility makes the masking of the smell of the ammonia yet more difficult. Patent JP2004067598 proposes that the odorizing agent that is capable of masking the smell of ammonia and that is unstable in ammonia be incorporated into the hydrogen peroxide composition to be mixed extemporaneously with the ammonia-containing composition.

In agribusiness, it is often desired to scent a product in order to create or increase a pleasant aroma or to add an aroma of freshness to a product. For example, EP 1 056 660 describes a drink receptacle cap which contains a segment molded in a synthetic material impregnated with a perfume, which diffuses the perfume so that the person perceives an aroma when he drinks.

In general, the prior art recommends, to mask a smell, creating a homogeneous mixture between the composition with the unpleasant smell and the masking agent. The inventors have now shown that, surprisingly, the masking of a smell and in particular of a very volatile smell, is more effective by deceiving, particularly by saturating, the gustatory or olfactory receptors of the user with the aid of a masking agent available through its inhomogeneous mixture with the base product, rather than with the aid of the same agent mixed homogeneously with the base product.

The object of the invention is particularly to mask or modify the olfactory or gustatory sensation generated by a base product in a user.

An objective of the invention is also to make it possible to perfume or scent a desired quantity of a base product contained in a package, without perfuming the rest of the product contained in the package. Another objective of the invention is to make it possible to perfume or scent successively small quantities of a base product extracted from a package with different aromas or perfumes or fragrances.

Another objective of the invention is to make it possible to perfume and/or scent a base product with a perfume or a scent that is generally considered to be incompatible with said base product or that is unstable in the base product, or that makes the base product unstable.

A particular objective of the invention is to cover or mask the smell of ammonia of a hair formulation, preferably of a permanent hair formulation, by using a perfume that is unstable or incompatible with one and/or the other of the two bases comprising said hair composition.

Within the meaning of the present invention, "unstable" means that the homogeneous mixture of said perfume or scent with the base product results in a significant modification of the organoleptic characteristics of said mixture.

Within the meaning of the present invention, "incompatible" means that the aromatic or fragrant composition cannot coexist with the base product for chemical reasons, for example because the coexistence induces structural modifications of the aromatic or fragrant composition or of the base product, for physical reasons, for example because the coexistence induces an undesirable change of solubility or a rheological modification of the base product, and/or for organoleptic reasons, in particular because of the possible formation of damaging products that are olfactorily or gustatorily undesirable.

"Package" within the meaning of the present invention means a receptacle in which the base product can be stored, and from which it can be extracted, expressed, taken out or poured, for its use, particularly by means of a delivery endpiece. Advantageously, the package is a bottle, in particular a flexible bottle that can be pressed in the hand to extract the product, a syringe, a tube, an aerosol or a pump. Advantageously, the package may be of the "airless" type or else a device of the type marketed under the brand SEMKIT™, or a package of the Mixpac™ System 25 type marketed by Mixpac or any package that those skilled in the art can adapt.

"Base product" within the meaning of the present invention means in particular a formulation to be perfumed or scented or whose smell must be masked, said formulation being able to be in fluid form, particularly cream, milk, lotion, gel, unguent, ointment, emulsion, gas, solid dispersion, liquid dispersion.

The invention therefore relates to a method for masking or modifying the olfactory or gustatory sensation generated in a user by a base product, characterized in that an aromatic or fragrant composition is released in a manner sequenced over time relative to the release of the base product, said aromatic or fragrant composition being contained in at least one breakable reservoir capable of releasing said composition at the desired moment(s). Advantageously, this reservoir comprises a breakable casing and a core comprising or consisting of said aromatic or fragrant composition; therefore, the casing encapsulates the volatile aromatic or fragrant composition and releases said composition when it is broken. Advantageously, this reservoir is a capsule, preferably as defined below.

According to a particular embodiment of the invention, the aromatic or fragrant composition forming the core and encapsulated in the casing is unstable and/or incompatible with the base product.

The release of the base product is a process that is capable of being spread over time. According to a preferred embodiment of the invention, a determined quantity of the base product is released. This determined quantity may be hereinafter indicated by the word "dose".

"Release of the base product" means the extraction of the base product, or of a dose of base product, from its package.

According to a first embodiment of the method according to the invention, at least one aromatic or fragrant composition contained in at least one reservoir is released before the start of the release of a base product.

According to a second embodiment of the method according to the invention, at least one first aromatic or fragrant composition contained in at least one reservoir is released by breaking said reservoir before the start of the release of the base product, and at least one second aromatic or fragrant composition, identical to or different from the first, contained in at least one other reservoir is released by breaking said reservoir at any moment during the release of a determined quantity of base product.

According to a third embodiment of the method according to the invention, at least one aromatic or fragrant composition contained in at least one reservoir is released by breaking said reservoir at any moment during the release of a desired quantity of the base product.

According to a fourth embodiment of the method according to the invention, a first aromatic or fragrant composition contained in at least one reservoir is released by breaking said reservoir at any moment during the release of the base product, and at least one second aromatic or fragrant composition, identical to or different from the first, contained in at least one other reservoir is released by breaking said reservoir after the end of the release of the desired quantity of base product.

According to a fifth embodiment of the method according to the invention, at least one aromatic or fragrant composition is released after the end of the release of the base product.

Within the meaning of the present invention, "before the release of the base product" relates to a time lag preceding the start of the release of the base product, going from 0.1 to 15 seconds, preferably 0.5 to 5 seconds, very preferably from 0.8 to 2 seconds.

Within the meaning of the present invention, "during the release of the base product" relates to the time lag necessary for the release of some or all of a dose of the base product.

Within the meaning of the present invention, "after the end of the release of the base product" relates to a time lag following the end of the release of the base product, going from 0.1 to 15 seconds, preferably 0.5 to 5 seconds, very preferably from 0.8 to 2 seconds.

According to a first embodiment of the invention, the base product according to the invention contains at least one main active pharmaceutical ingredient, a pharmaceutical composition or a medication.

According to a second embodiment of the invention, the base product contains at least one active cosmetic ingredient, and preferably is a cosmetic care cream, a hair product of the shampoo type or a hair coloring product, or a product for depilatory purposes of the depilatory cream type.

According to a third embodiment, the base product is a food, agribusiness, nutraceutical or dietetic product, preferably yogurt, sauce or drink.

According to a fourth embodiment, the base product is a hygiene product, in particular personal hygiene, particularly by mouth, domestic hygiene or industrial hygiene, particularly a detergent, fabric softener, a bactericide.

According to a fifth embodiment, the base product is an insecticide product or an active phytopharmaceutical ingredient.

The invention also relates to a device for applying the above method.

According to a particular embodiment, the object of the invention is a device comprising an aromatic or fragrant composition contained in a reservoir, said composition being designed to perfume or scent some or all of a base product contained in a package, and any appropriate means of breaking said reservoir before the release of a desired quantity of base product, before and during the release of some or all of the desired quantity of the base product, during some or all of the release of a desired quantity of base product, during and/or after the end of the release of the desired quantity of base product.

Advantageously, the device comprises an aromatic or fragrant composition designed to perfume or scent some or all of a base product extracted from a package, said device being adaptable to the orifice for extraction of the base product from said package, comprising an orifice for releasing the aromatic or fragrant composition and the base product, where necessary mixed together, and comprising said aromatic or fragrant composition contained in at least one reservoir (5).

"Device that can be adapted to the orifice for extraction from a package", within the meaning of the present invention, means a device comprising adaptation means, particularly screwing, clipping, bonding, interlocking, crimping means compatible with the structure of the orifice for extraction from the package.

Advantageously, the device according to the invention is an end-piece that can be adapted to the orifice for extraction of the base product from the package, containing at least one reservoir of aromatic or fragrant composition. According to a particular embodiment, the device of the invention is characterized in that said device comprises at one of its ends a female portion that can be adapted to an orifice for extraction from the package consisting of a male end-piece and, at another distal end, an orifice for extraction of the volatile aromatic or fragrant composition and of the base product, where necessary mixed together.

Advantageously, each reservoir contained in the device of the invention comprises a breakable casing and a core comprising or consisting of said volatile aromatic or fragrant composition and the aromatic or fragrant composition is released by breaking this casing. Preferably, this reservoir is a capsule. Preferably, the casing of the reservoir is broken at a pressure greater than 1 kg, preferably lying between 1 and 2.5 kg.

Preferably, the reservoir (5) is broken either by the placing in contact of the reservoir (5) and of the base product (7) extracted from the package, or by the actuation of a means for breaking the casing that may or may not be contained in the device of the invention.

According to a first embodiment, the breakage of the casing of the reservoir results from the placing in contact of the reservoir and of the base product extracted from the package. In this embodiment, the casing is broken either by the product, by a chemical action, or under the effect of the passage of the product.

According to a second embodiment, the casing is broken manually by the user of the device; the breakage of the reservoir then results from the mechanical action applied by the user on the reservoir.

According to a third embodiment, the casing is broken by a means for breaking the casing, said breaking means being contained in the device of the invention. According to a particular embodiment of the invention, this breaking means may be of the needle type, for example actuated by a piston, or else of the type in particular of a shearing means, preferably of the static mixer type, of a baffle, of a convergent means, of an abrasive coating, of an abutment.

According to one embodiment of the invention, the device of the invention can be adapted to the orifice that makes it possible to extract the base product from its package.

Advantageously, the device of the invention comprises a means for releasing the aromatic or fragrant composition and the base product, and optionally a means for mixing said aromatic or fragrant composition with the base product. Advantageously, this releasing means is an extraction orifice situated at a distal end of the device relative to its end that can be adapted to the orifice for extraction from the package.

According to a particular embodiment, the device of the invention is a device for sequenced release of at least one aromatic or fragrant composition and of the base product, wherein the aromatic or fragrant composition is released before the start of the release of the product. In this embodiment, at least one of the reservoirs contained in the device is broken before the product is delivered to the user. This embodiment has the advantage of releasing the volatile product before the user of the base product has been in contact with the smell or the scent of the base product; therefore, the first olfactory or gustatory sensation of the user is that provided by the content of the broken reservoir. In a preferred variant of this embodiment, the device does not comprise a means for mixing the aromatic or fragrant composition with the base product.

According to a second particular embodiment, the aromatic or fragrant composition is released before the start of the release of the product, and also during the release of the base product. In this embodiment, at least one of the reservoirs contained in the device is broken before the product is delivered to the user, and at least one other reservoir is broken during the release of the base product, either by mechanical action, or by chemical action of the base product on the casing of the reservoir. In this embodiment, the first olfactory or gustatory sensation of the user is that provided by the content of the first broken reservoir(s) and this sensation is prolonged during some or all of the release of the base product by the breakage of other reservoirs, thereby masking the sensation that would have been generated by the release of said base product that is neither scented nor perfumed.

According to a third particular embodiment, the aromatic or fragrant composition is released by breaking at least one reservoir during the release of the base product, for a direct action of masking the scent or the taste of the base product. In a preferred variant of this embodiment, the device comprises a means for mixing the aromatic or fragrant composition with the base product.

According to a fourth particular embodiment, the aromatic or fragrant composition is released during the release of the base product and at least one reservoir is broken after the end of the release of the desired quantity of the base product. This embodiment has the advantage of directly masking the scent or the taste of the base product, and of continuing this masking action by prolonging the olfactory or gustatory sensation of the user with the aromatic or fragrant composition contained in the device.

According to a fifth particular embodiment, no reservoir is broken before or during the release of the base product, and at least one reservoir is broken after the end of the release of the desired quantity of the base product. This embodiment has the advantage of modifying or masking the olfactory or gustatory sensation of the user with the aromatic or fragrant composition contained in the device. This fifth embodiment is particularly preferred for the masking of the smell of a base product containing ammonia. In this embodiment, the base product is not likely to chemically break the casing of the reservoir.

According to one embodiment, the aromatic or fragrant composition is unstable and/or incompatible with said base product (7).

Finally, the subject of the invention is a product obtained by the method mentioned hereinabove, characterized in that it comprises an inhomogeneous, that is to say not intimate, mixture of a base product and of an aromatic or fragrant composition, the aromatic and fragrant composition and the base product being compatible or incompatible.

According to a preferred embodiment of the invention, the device of the invention is a single-use device.

A further subject of the invention is a device placed on a package of base product, in a movable or immovable manner.

Finally, the subject of the invention is a method for perfuming or scenting successively a base product (7) contained in a single package with different aromatic or fragrant compositions, in which a first device (1) according to the invention, comprising a first aromatic or fragrant composition, is adapted to the package, and a first dose of a base product is extracted, then at least one second device (1) according to the invention, comprising a second aromatic or fragrant composition, is adapted to said package, if necessary after removal of the first device (1), and at least one second dose of said base product is extracted.

"Capsule", within the meaning of the present invention, means any device that can serve as a reservoir or a means for storing a scent or art aromatic composition, irrespective of its size or shape. Advantageously, the word "capsule" relates to a device comprising a casing and a core; preferably the thickness of the casing lies between approximately 30 and approximately 100 µm, preferably from 50 to 65 µm. Preferably the casing represents from 2 to 30% of the weight of the capsule, preferably from 2.5 to 20%, advantageously from 3 to 8%. The core of the capsule comprises a scent or an aromatic or fragrant composition, that preferably consists of a mixture of molecules that are hydrophobic or partially soluble in ethanol or molecules placed in the form of water/oil, oil/water, oil/water/oil emulsion; preferably, the core consists of aromatic compositions, particularly the aromatic, terpene-based and/or sesquiterpene-based hydrocarbons and more particularly the essential oils, alcohols, aldehydes, phenols, carboxylic acids in their various forms, ethers and aromatic acetals, nitrous heterocycles, ketones, sulfurs, aromatic disulfides and mercaptans. It may also comprise one or more molecules or extracts for cosmetic, pharmaceutical, food or other use, depending on the envisaged application. According to a particular embodiment of the invention, the core of the capsule contains a solvent comprising triglycerides, particularly caprylic and capric acid triglycerides, triglyceride mixtures of the vegetable oil type, olive, sunflower, maize, peanut, grapeseed, wheatgerm oil, mineral oils and silicone oils; the quantity of lipophilic solvent in the core of a capsule used according to the invention is of the order of 0.01 to 90% of the weight of the capsule, preferably from 25 to 75%; the core may also comprise one or more agents called weights as used in aromatic emulsions, of the damar gum type, ester gum type wood resins, saccarose acetoisobutyrate (SAIB) or brominated vegetable oils. The function of these weights is to adjust the density of the liquid core. The core may also comprise one or more sweeteners, which may be provided in the form of a solution or suspension in ethanol. Not exclusively, these include aspartame, NHDC, sucralose, acesulfame, neotame. The core may also comprise one or more aromatic agents called sensate, which provide either a refreshing effect or a hot effect in the mouth. These include in particular as a refreshing agent, menthyl succinate and its derivatives, particularly Physcool @ marketed by the Applicant. Mention will be made as a hot effect agent of vanillyl ethyl ether. The present invention also includes, in the word capsule, spherical capsules and nonspherical capsules, several millimeters in diameter or several microns in diameter. The capsules used according to the invention are preferably hard to the touch, and may break under the effect of a mechanical force, for example a pressure, or under the effect of a means of chemical breakage. Preferably, the capsules according to the invention have a hardness of the order of 1 to 5 kg/cm². According to one embodiment, the capsule used according to the invention is spherical or substantially spherical, preferably perfectly spherical. It has a variable diameter, preferably from 1 to 7 mm in diameter. This diameter will depend on the use and may be easily chosen by those skilled in the art. The weight of a capsule according to the invention is variable, it may be from 0.5 to 170 mg. In a preferred embodiment, the capsule according to the invention has a diameter of 4.5 to 5.5 mm, and a weight of 45 to 80 mg. According to a preferred embodiment, the capsule is as described in EP1455596, included here as reference. According to another embodiment, the capsule used in the device according to the invention is a capsule whose casing contains gellan or gelatine or any appropriate material, and preferably a capsule as described in international patent application PCT/EP05/09226, and a core formed of a volatile aromatic or fragrant composition. According to yet another embodiment, the capsule used in the device according to the invention is of the type of those described in international patent application PCT/EP05/09227, and in particular a humidity-resistant capsule; advantageously, the casing of the capsule is covered with a coating of the ethylcellulose type.

The invention will be better understood on reading the following detailed examples, which illustrates in a nonlimiting manner a particular embodiment of the invention and is read with respect to FIG. 1.

FIG. 1 represents a profile view of a device 1 according to the invention and of a package 2 of the base product.

The device 1 according to the invention, which may have any shape and is not limited to the graphic representation of FIG. 1, comprises reservoirs 5. In the embodiment of FIG. 1, these reservoirs are capsules consisting of a casing 6 and a core consisting of the aromatic or fragrant composition.

A base product 7 is situated in the package 2. This package 2 comprises an extraction orifice 3, or end-piece, capable of delivering the base product for the purpose of its use. The device 1 comprises an end 4 that can be adapted to the extraction orifice 3. The user may manually adapt the device 1 to the end-piece 3. According to a particular embodiment of the invention, not shown, the device 1 is attached to the end-piece 3 prior to the use of the base product.

When carrying out the manipulations necessary to deliver the base product, the user expresses the base product 7 from the package 2 via the end-piece 3 on which the device 1 is placed. The product expressed through the end-piece 3 comes into contact with the capsules 5. The capsules break under the mechanical action of the base product 7 that is propelled by the user into contact with the capsules 5 with sufficient pressure to break them, or under the chemical effect of solubilization of the casing by the base product, or under the effect of a breaking means present in the device, or under the effect of the mechanical pressure of the user on the device. Some or all of the capsules 5 may break. The capsules 5 may break simultaneously or successively. When they break, they release the aromatic or fragrant composition that they contain, which can mix with the base product 7. In a particular embodiment of the invention, not shown, the device 1 comprises a means of mixing the base product and the aromatic or fragrant composition, said means of mixing comprising mixture elements. Depending on the number and size of the mixture elements, a more or less homogeneous mix is obtained, which allows those skilled in the art to obtain the desired effect of coverage or perfuming.

EXAMPLE 1

A simple bayonet static mixer of the MA STATOMIX type made of polypropylene marketed by MIXPAC Systems, furnished with mixture elements, is used. The mixture elements are cut so as to be able to cause the breakable capsules marketed by MANE to enter in the desired quantity, namely the sufficient quantity to obtain a dose of perfume identical to that which would be used in a commercial intimate mixture product. The identification of this dose is within the competence of those skilled in the art.

The hair coloring product is prepared in a flexible plastic bottle with a sectile cap of the type marketed by l'Oréal for its Excellence Crème™ products of l'Oréal Paris™, or by Henkel for Schwartzkopf Vision Color Relief™, or else by Clairol for Perfect Blondes™, by Eugène Perma for Eugène Color™ or Keranove™, and by Mandom for Gatsby™. The hair coloring product is obtained by mixing the ammonia-containing base on the one hand and the oxidizing portion on the other hand, then stirring the mixture. The sectile cap is cropped, and the bottle then becomes a package of the base product of which the hair coloring mixture is made. Before delivery, the static mixer furnished with the capsules is adapted to the end-piece thus opened.

The mixture of base product is expressed from the flexible plastic bottle or boiling vessel by pressure on the walls of said bottle. The mixture comes into contact in the mixer with the capsules. Under the pressure of the product, the capsules break successively when the product passes. The base product and the liquid perfume released by the capsule are sheared by the mixture elements and then expressed.

EXAMPLE 2

A static mixer of the MA STATOMIX type made of polypropylene marketed by MIXPAC Systems, furnished with capsules containing an aromatic or fragrant composition, is adapted to the end-piece of a MIXPAC Systems S25 pistol furnished with 50 ml two-compartment cartridges. Each portion of the formulation is present in its compartment; it is sufficient to connect the device (twist-lock) and to install the cartridge in the pistol furnished with the button corresponding to the chosen cartridge. The pressure on the trigger of the pistol actuates the pistons which inject the two portions of the formulation into the device of the invention. The advantage provided by the use of the pistol is to be able to use products with a very viscous base.

The invention claimed is:

1. A device (1) in combination with a package (2) wherein, said device (1) has a female portion (4) at one distal end and an orifice for extraction (8) at another distal end, and comprises at least one breakable reservoir and a means for breaking said reservoir, said reservoir comprising at least one aromatic or fragrant composition;

said package (2) comprises a base product and a male end-piece orifice (3) for extraction of said base product; and said device (1) is configured for removable placement on the package (2) by adapting the female portion (4) of the device (1) to said male end-piece orifice (3) for extraction of the base product from said package (2).

2. The device (1) in combination with a package (2) as claimed in claim 1, wherein said reservoir comprises a breakable casing and a core comprising said aromatic or fragrant composition.

3. The device (1) in combination with a package (2) as claimed in claim 1, wherein said reservoir is a capsule.

4. The device (1) in combination with a package (2) as claimed in claim 2, wherein the reservoir is broken either by the placing in contact of the reservoir and of the base product extracted from the package, or by a mechanical action applied by a user, or by the actuation of a means for breaking the casing contained in the device (1) selected from the group consisting of a means for shearing, a baffle, a convergent means for breaking, an abrasive coating, and an abutment.

5. The device (1) in combination with a package (2) as claimed in claim 1, further comprising a means for mixing said aromatic or fragrant composition with said base product.

6. The device (1) in combination with a package (2) as claimed in claim 1, wherein said aromatic or fragrant composition is unstable and/or incompatible with said base product.

7. The device (1) in combination with a package (2) as claimed in claim 1, wherein said base product is in fluid form selected from the group consisting of cream, milk, lotion, gel, unguent, ointment, emulsion, gas, solid dispersion, and liquid dispersion.

8. The device (1) in combination with a package (2) as claimed in claim 1, wherein the base product contains at least one main active pharmaceutical ingredient, a pharmaceutical composition or a medication; or at least one active cosmetic ingredient, for the purpose of treatment or for hair selected from the group consisting of shampoo and hair coloring product, or of the depilatory cream; or the base product is a food, agribusiness, nutraceutical or dietetic product; or the base product is a hygiene product selected from the group consisting of personal hygiene domestic hygiene or industrial hygiene selected from the group consisting of a detergent, fabric softener, and a bactericide; or the base product contains a phytopharmaceutical product or an insecticide.

9. The device (1) in combination with a package (2) as claimed in claim 2, wherein said reservoir is broken at a pressure lying between 1 and 2.5 kg.

10. The device (1) in combination with a package (2) as claimed in claim 3, wherein said capsule comprises a casing and a core, the casing representing from 2 to 30% of the weight of the capsule.

11. The device (1) in combination with a package (2) as claimed in claim 3, wherein said capsule has an hardness from 1 to 5 kg/cm$^2$.

12. The device (1) in combination with a package (2) as claimed in claim 3, wherein the capsule is spherical and has a diameter of 4.5 to 5.5 mm.

* * * * *